United States Patent [19]

Picart

[11] Patent Number: 4,680,411

[45] Date of Patent: * Jul. 14, 1987

[54] PYRANO[2,3-G]INDOLES USEFUL AS ANTI-ULCEROUS, ANTI-INFLAMMATORY AND ANTALGIC AGENT

[75] Inventor: Francois Picart, Dijon, France

[73] Assignee: Societe de Recherches Industrielles, Paris, France

[*] Notice: The portion of the term of this patent subsequent to Mar. 13, 2001 has been disclaimed.

[21] Appl. No.: 588,566

[22] Filed: Mar. 12, 1984

Related U.S. Application Data

[62] Division of Ser. No. 276,643, Jun. 23, 1981, Pat. No. 4,436,915.

[30] Foreign Application Priority Data

Jun. 26, 1980 [FR] France ............................ 80 14246

[51] Int. Cl.$^4$ ................... C07D 491/06; A61K 31/40
[52] U.S. Cl. ................................................ 548/430
[58] Field of Search ..................... 548/430; 424/274; 514/411

[56] References Cited

U.S. PATENT DOCUMENTS

| | | | |
|---|---|---|---|
| 3,812,112 | 5/1974 | Kimura et al. | 548/430 |
| 4,436,915 | 5/1984 | Picart | 548/432 |

FOREIGN PATENT DOCUMENTS

| | | | |
|---|---|---|---|
| 43752 | 1/1982 | European Pat. Off. | 548/430 |
| 2267777 | 11/1975 | France . | |

OTHER PUBLICATIONS

Kim et al., Chem. Abst. 98:24489n.
Bohze et al., Chem. Abst. 96:162677k.
Chakraborty et al., Chem. Abst. 79:66631u.

Primary Examiner—Robert Gerstl
Assistant Examiner—Cecilia Shen
Attorney, Agent, or Firm—Dennison, Meserole, Pollack & Scheiner

[57] ABSTRACT

The present invention relates as new industrial product to a derivative of pyrano-indole chosen from the group constituted by:
(i) the pyrano[2,3-g]indoles of general formula:

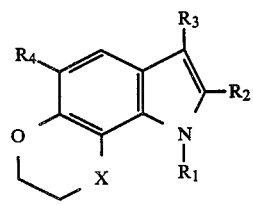

in which:
X represents a group

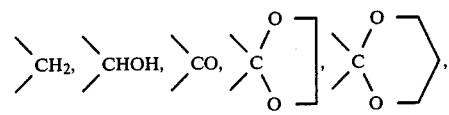

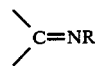

(where R is a lower alkyl group, OH, lower alkoxy, tosyloxy, $NH_2$) or

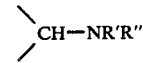

(where R' and R", which are identical or different, each represent H or a lower alkyl);
$R_1$ represents an atom of hydrogen, a lower alkyl group, or $COY_1$
(where $Y_1$ is a lower alkyl group, an amino acid group $CH_2CH(COOH)$ $NH_2$ or an aminoalkylene group $-(CH_2)_n-NR'R"$ in which is a whole number between 1 and 4 and R' and R" are defined as hereinabove);
$R_2$ represents an atom of hydrogen, or a $COY_2$ group (where $Y_2$ is OH or lower alkoxy;
$R_3$ represents an atom of hydrogen, an atom of halogen, a CHO group, lower alkyl, $CF_3$, $(CH_2)_nNR'R"$ or CO-CONR'R"
(where n, R' and R" are defined as hereinabove), and
$R_4$ represents an atom of hydrogen, an atom of halogen, an OH group, lower alkyl, lower alkoxy, $CF_3$ or NR'R"
(where R' and R" are defined as hereinabove);
(ii) the pyrano [3,2-f]indoles of general formula:

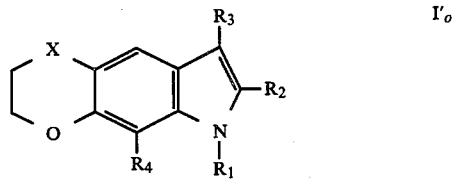

where X, $R_1$, $R_2$, $R_3$ and $R_4$ are defined as hereinabove; and
(iii) their acid addition salts.

The invention also relates to the process for preparing this derivative and to its application in therapeutics.

8 Claims, No Drawings

PYRANO[2,3-G]INDOLES USEFUL AS ANTI-ULCEROUS, ANTI-INFLAMMATORY AND ANTALGIC AGENT

This application is a division of application Ser. No. 276,643, filed June 23, 1981, now U.S. Pat. No. 4,436,915.

The present invention relates as new industrial product to a pyrano-indole derivative. It also relates to the process for preparation thereof and to its application in therapeutics, particularly as anti-ulcerous, anti-inflammatory and antalgic agent.

The derivative according to the invention is chosen from the group constituted by:

(i) the pyrano[2,3-g]indoles of general formula:

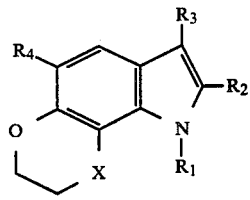

in which

X represents a group

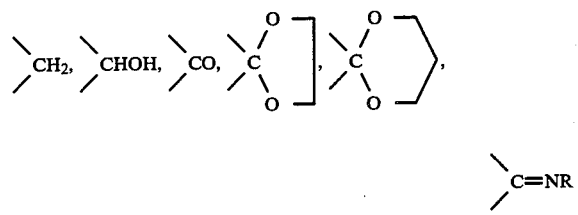

(where R is a lower alkyl group, OH, lower alkoxy, tosyloxy, $NH_2$) or

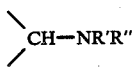

(where R' and R", which are identical or different, each represent H or a lower alkyl);

$R_1$ represents an atom of hydrogen, a lower alkyl group, or $COY_1$
 (where $Y_1$ is a lower alkyl group, an amino acid group $CH_2CH(COOH)NH_2$ or an aminoalkylene group $-(CH_2)_n-NR'R''$ in which n is a whole number between 1 and 4 and R' and R" are defined as hereinabove);

$R_2$ represents an atom of hydrogen, or a $COY_2$ group (where $Y_2$ is OH or lower alkoxy;)

$R_3$ represents an atom of hydrogen, an atom of halogen, a CHO group, lower alkyl, $CF_3$, $(CH_2)_nNR'R''$ or CO—CONR'R"
 (where n, R' and R" are defined as hereinabove) and $R_4$ represents an atom of hydrogen, an atom of halogen, an OH group, lower alkyl, lower alkoxy, $CF_3$ or NR'R"
 (where R' and R" are defined as hereinabove);

(ii) the pyrano[3,2-f]indoles of general formula:

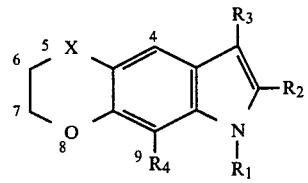

where X, $R_1$, $R_2$, $R_3$ and $R_4$ are defined as hereinabove; and (iii) their acid addition salts.

Lower alkyl group is understood here to mean a hydrocarbon radical with straight or branched chain and with 1-4 carbon atoms. Lower alkoxy group is understood to mean a straight or branched chain group with 1-4 carbon atoms. From suitable lower alkyl and lower alkoxy groups, particular mention may be made of $CH_3$, $CH_2CH_3$, $CH_2CH_2CH_3$, $CH(CH_3)_2$, $C(CH_3)_3$, $OCH_3$, $OCH_2CH_3$, $OCH(CH_3)_2$ and $OC(CH_3)_3$.

Atom of halogen is understood here to mean an atom of fluorine, chlorine, bromine or iodine, the preferred atoms of halogen being bromine and chlorine.

A certain number of pyrano-indole derivatives according to the invention have been given, in non-limiting manner, in Tables I and II hereinbelow.

The process for preparing a pyrano-indole compound according to the invention is illustrated by the reactional mechanisms of diagram 1 hereinbelow. This process is characterised in that:

(a) a pyrano-indole-carboxylate of formula IX is prepared as follows:
 (i) the aldehyde of formula VII (where X and $R_4$ are defined as hereinabove) is reacted with ethyl azidoacetate in the presence of a lower alcohol (particularly $C_2H_5OH$ and preferably $CH_3OH$) and of an alkali metal (particularly Na and K) at a temperature of $-5°$ C. to $+5°$ C. (preferably $0°$ C.) for at least 3 hours, to obtain an azide of formula VIII, and
 (ii) said azide VIII is cyclized in the presence of an inert solvent (preferably an aromatic solvent such as benzene, toluene, xylene) at the reflux temperature of the reaction medium for at least 1 hour, to obtain said pyrano-indole-carboxylate IX (which is a derivative of formula $I_o$ where $R_1=R_3=H$ and $R_2$ which represents a carboxylate radical is preferably $COOCH_3$), then (b) if necessary, said pyrano-indole-carboxylate is converted into corresponding acid, esters and amides by saponification, transesterification and transamidification, respectively.

The best mode of preparing all the compounds of formulae $I_o$ and $I'_o$ (which is also illustrated in diagram 1 hereinbelow) consists in (c) saponifying the ester IX to obtain the corresponding acid X (which is a derivative of formula $I_o$ where $R_1=R_3=H$ and $R_2=COOH$), (d) decarboxylating said acid X by means of a catalyst, preferably copper chromite prepared from CuO and $Cr_2O_3$) in the presence of inert solvent (preferably quinoline at $180°-200°$ C. under 1 atmosphere) to obtain (i) a mixture of compounds XI and XI' when $R_4=H$ which is separated in particular by chromatography on silica and (ii) compound XI only when $R_4$ is different from H, then (e) if necessary, introducing at least one of the groups $R_1$ and $R_3$, different from H to obtain, from XI and XI' respectively the compounds XII and XII''; and, if need be, introducing the group $R_4$ different from H to obtain the compound XII' from compound XI'.

The acid $R_2=COOH$ group may of course be esterified, amidified and decarboxylated.

The compounds VII, which intervene as raw materials in the process of synthesis of the pyrano-indoles of formulae $I_o$ and $I'_o$, may be prepared according to a method known per se, by application of conventional reactional mechanisms.

According to the invention, several routes are recommended for synthesis thereof, as a function of the nature of group X. These routes are illustrated by diagrams 2 and 3 hereinbelow.

Route A shown in diagram 2 envisages obtaining a particular derivative VII when the group X is $CH_2$. In a first variant, (when X is $CH_2$ and $R_4$ is H), the 6-bromo-chroman of formula Ia is subjected to a reaction with CuCN in the presence of dimethylamine (DMA) to yield the corresponding 6-cyano-chroman, which is then subjected to a reaction of reduction, particularly in the presence of Ni and of $NaH_2PO_2$ to yield the 6-chromanylcarbaldehyde derivative of formula IIa. In a second variant (when X is $CH_2$ and $R_4$ is different from H), a 6-bromo-chroman substituted in 8 position, of formula Ib is subjected to a reaction with an organolithian (preferably butyllithium) within the dimethylformamide, to obtain a 5-chromanyl carbaldehyde substituted in 8 position, of formula IIb.

Route B, shown in diagram 3, envisages obtaining a particular derivative VII (in which X is

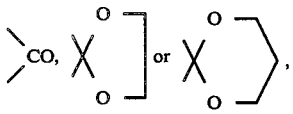

$R_4$ being any). This route consists in reacting a 5-bromo-chromanone of formula III by means of $HOCH_2CH_2OH$ or $HOCH_2CH_2CH_2OH$ in an inert solvent (preferably an aromatic solvent such as benzene, toluene and xylene) in the presence of p-toluene-sulfonic acid (ATPS), to obtain a brominated derivative of IV where X is

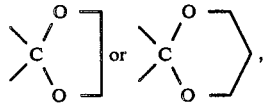

in subjecting the product IV thus obtained to a reaction with an organolithian (preferably butyllithium) within the dimethylformamide to replace the bromo group in CHO group and obtain a derivative of formula V where X is

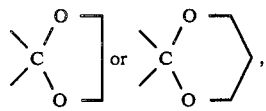

this acetal derivative being, if necessary, converted into 6-formyl chromanone derivative of formula VI by acid hydrolysis.

The intermediate compounds IIb, IV, V and VI, which intervene in the synthesis of the pyrano-indole derivatives of the invention, are novel.

Further advantages and features of the invention will be more readily understood on reading the following examples of preparation given by way of non-limiting illustration. "Preparations I-XI" relative to obtaining the raw materials will be found hereinafter, then Examples 1-31 given in Tables I and II hereinbelow.

PREPARATION I 6-bromo-8-chloro-chroman (I $b_1$)

To the amalgam of zinc—prepared from 1280 g (19.7 gram-atoms) of zinc, 128 g ($5.4 \times 10^{-1}$M) of mercurous chloride, 64 cm$^3$ of concentrated hydrochloric acid and 1900 cm$^3$ of water—are added, in order, 1000 cm$^3$ water, 1500 cm$^3$ of concentrated hydrochloric acid, 3500 cm$^3$ of toluene and 640 g (2.45M) of 6-bromo-8-chloro-4-chromanone (III$_2$). The mixture is refluxed for 1 hour and, after cooling and decantation, it is extracted with ether and washed in water up to neutrality. 305 g (yield=50%) of expected product are thus isolated.

B.p.$_{0.01}$=128° C.

Analysis $C_9H_8OBrCl$: % calculated: C 43.68, H 3.23, Br 32.29. % found: C 43.5, H 3.2, Br 32.0.

PREPARATION II 6-bromo-8-methoxy-chroman (Ib$_2$)

According to the process of preparation I, from the amalgam of zinc prepared form 915 g (14 gram-atoms) of zinc, 91 g ($3.8 \times 10^{-1}$M) of mercurous chloride in 46 cm$^3$ of concentrated hydrochloric acid and 1350 cm$^3$ of water, after addition of 700 cm$^3$ of water, 1100 cm$^3$ of concentrated hydrochloric acid, 2500 cm$^3$ of toluene and 450 g (1.8M) of 6-bromo-8-methoxy-4-chromanon (III$_1$), 200 g (yield=47%) of the expected product are obtained.

M.p.=67° C.

Analysis $C_{10}H_{11}O_2Br$: % calculated: C 49.42, H 4.52, O 13.16, Br 32.88. % found: C 49.4, H 4.5, O 13.5, Br 32.6.

PREPARATION III 8-chloro-chroman-6-carbaldehyde (IIb$_1$)

72 g ($2.9 \times 10^{-1}$M) of dihalochroman Ib$_1$ dissolved in 250 cm$^3$ of anhydrous ether are added slowly and with stirring in $2.9 \times 10^{-1}$M of n-butyllithium in 320 cm$^3$ of anhydrous ether. The temperature is maintained at $-70°$ C. for 6 hours then 31 g ($3.8 \times 10^{-1}$M) of N,N-dimethylformamide dissolved in 150 cm$^3$ of anhydrous ether are added drop by drop. The reaction mixture is further maintained at the same temperature for 12 hours, with stirring, then—after return to ambient temperature—it is poured on glacial water. After acidification with 5N hydrochloric acid, extraction with ether and evaporation, 54 g (yield=95%) of 8-chloro-chroman-6-carbaldehyde are isolated.

m.p.=51° C.

Analysis $C_{10}H_9O_2Cl$: % calculated: C 61.11, H 4.57, O 16.27, Cl 18.03. % found: C 61.2, H 4.6, O 16.3, Cl 18.0.

PREPARATION IV 8-methoxy-chroman-6-carbaldehyde (IIb$_2$)

The procedure is as according to the method described for preparation III, but maintaining the temperature at −50° C. From 186 g (7.7×10$^{-1}$M) of bromomethoxy-chroman Ib$_2$ in 500 cm$^3$ of anhydrous ether and 7.7×10$^{-1}$M of n-butyllithium in 650 cm$^3$ of anhydrous ether, and after addition of 78 g (1.1M) of N,N-dimethylformamide in 200 cm$^3$ of anhydrous ether and recrystallisation in isopropyl ether, 75 g (yield=51%) of expected compound are isolated.

m.p.=81° C.

Analysis C$_{11}$H$_{12}$O$_3$: % calculated: C 68.77, H 6.24, O 24.97. % found: C 69.0, H 6.3, O 25.2.

PREPARATION V 6-bromo-8-methoxy-4-chromanon (III$_1$)

34 g (3.5×10$^{-1}$M) of phosphoric acid are added—at 0° C.—in a mixture containing 475 cm$^3$ of anhydrous benzene and 56 g (4×10$^{-1}$M) of phosphoric anhydride. After having boiled for 4 hours, 83 g (3×10$^{-1}$M) of 3(4-bromo-2-methoxy-1-phenoxy)-propionic acid are slowly added. The mixture is maintained at boiling point for 12 hours, then, after cooling, poured onto glacial water, treated with 5N hydrochloric acid and extracted with ether. After usual treatment and recrystallisation of the solid obtained in ethanol, 67 g (yield=86%) of expected compound are isolated.

m.p. 137° C.

Analysis C$_{10}$H$_9$O$_3$Br: % calculated: C 46.73, H 3.50, O 18.66, Br 31.09. % found: C 46.7, H 3.5, O 18.7, Br 31.3.

PREPARATION VI 6-bromo-8-chloro-4-chromanon (III$_2$)

A mixture of 279 g (1M) of 3-(4-bromo-2-chloro-1-phenoxy)-propionic acid and 127 g (1.3M) of concentrated sulfuric acid is taken for 2 hours to 70°–80° C. The reaction mixture is then poured onto glacial water, extracted with ether, washed with a dilute solution of ammonia then with water. 183 g (yield=70%) of expected product is finally obtained.

m.p.=109° C.

Analysis C$_9$H$_6$O$_2$BrCl: % calculated: C 41.34, H 2.29, O 12.23. % found: C 41.3, H 2.4, O 12.1.

PREPARATION VII

Dioxolan of 6-bromo-8-methoxy-4-chromanon (IV$_1$)

10 g (3.9×10$^{-2}$M) of 4-chromanon III$_1$, 24 g (3.9×10$^{-1}$M) of ethylene glycol and 0.3 g (1.7×10$^{-3}$M) of paratoluene sulfonic acid in 200 cm$^3$ of anhydrous toluene are taken to boiling point for 7 hours in Dean and Stark apparatus. The reaction mixture is then poured onto glacial water, extracted with ether and the solid obtained is recrystallised in an ethyl alcohol-ether mixture. 9.6 g (yield=82%) of expected product are obtained.

m.p.=104° C.

Analysis C$_{12}$H$_{13}$O$_4$Br: % calculated: C 47.88, H 4.31, O 21.25, Br 26.54. % found: C 47.8, H 4.5, O 21.3, Br 26.4.

PREPARATION VIII

Dioxolan of 6-bromo-8-chloro-4-chromanon (IV$_2$)

Similarly, 30 g (1.1×10$^{-1}$M) of 4-chromanon (III$_2$), 71 g (1.1M) of ethylene glycol and 0.2 g (1.1×10$^{-3}$M) of paratoluene sulfonic acid in 200 cm$^3$ of toluene, lead, after recrystallation in a benzene-isopropyl ether mixture, to 34 g (yield=97%) of expected product.

m.p.=94° C.

Analysis C$_{11}$H$_{10}$O$_3$BrCl: % calculated: C 43.25, H 3.27, O 15.70. % found: C 43.2, H 3.2, O 15.6.

PREPARATION IX 4-dioxolano-8-methoxy-chroman-6-carbaldehyde (V$_1$)

177 g (5.9×10$^{-1}$M) of dioxolan IV$_1$ dissolved in 500 cm$^3$ of anhydrous ether are added slowly at −70° C. to 5.9×10$^{-1}$M of n-butyllithium in 570 cm$^3$ of anhydrous ether. After addition, the medium is maintained for 6 hours at −70° C. and 56 g (7.7×10$^{-1}$M) of N,N-dimethylformamide dissolved in 300 cm$^3$ of anhydrous ether are added drop by drop. The reaction mixture is maintained for 12 hours at −70° C. then, after return to ambient temperature, poured onto glacial water. After extraction with chloroform, recrystallisation of the solid obtained in ethanol, 133 g (yield=90%) of expected product are isolated.

m.p.=167° C.

Analysis C$_{13}$H$_{14}$O$_5$: % calculated: C 62.43, H 5.59, O 31.96. % found: C 61.2, H 5.6, O 31.2.

PREPARATION X 8-chloro-4-dioxolano-chroman-6-carbaldehyde (V$_2$)

By operating as indicated in preparation IX, and from 45 g (1.5×10$^{-1}$M) of dioxolan IV$_2$, 31 g (yield: 84%) of expected product are obtained after recrystallisation in benzene.

m.p.=133° C.

Analysis C$_{12}$H$_{11}$O$_4$Cl: % calculated: C 56.62, H 4.32, O 25.12. % found: C 55.3, H 4.5, O 24.6.

PREPARATION XI 8-methoxy-4-oxo-chroman-6-carbaldehyde (VI$_1$)

To 34 g (1.4×10$^{-1}$M) of dioxolan V$_1$ in 700 cm$^3$ of ethyl alcohol are added—slowly and at ambient temperature—90 cm$^3$ of concentrated hydrochloric acid. The mixture is maintained for 1 hour under stirring then poured onto glacial water and extracted with ether. After recrystallisation of the solid obtained from ethyl alcohol, 26 g (yield: 91%) of expected product are obtained (m.p.=139° C.).

Analysis C$_{11}$H$_{10}$O$_4$: % calculated: C 64.10, H 4.85, O 31.03. % found: C 64.5, H 4.9, O 30.1.

EXAMPLE 1

7,8,9-trihydro-pyrano[2,3-g]indole-2-carboxylate of methyl

To a methanol solution of sodium methylate [1.4 g of Na (6×10$^{-2}$ gram-atoms) in 30 cm$^3$ of anhydrous methanol], are added, at 0° C., 4.5 g (2.8×10$^{-2}$M) of 6-formyl-chroman, dissolved in 10 cm$^3$ of anhydrous methanol. 7.2 g (5.6×10$^{-2}$M) of ethyl azidoacetate are then poured, drop by drop, at 0° C. and with stirring, in 10 cm$^3$ of anhydrous methanol. After having maintained the temperature at 0° C. for 6 hours, the reaction mixture is poured on glacial water and the azide is retained by filtration.

In 30 cm$^3$ of xylene taken to boiling point, the azide dissolved in 150 cm$^3$ of xylene is added with stirring. The addition terminated, stirring and reflux are maintained for 5 hours. After elimination of the xylene, the solid residue obtained is recrystallised from an isopropyl ether-benzene mixture and 2.7 g (yield=42%) of expected product are obtained.

m.p.=163° C.

Analysis $C_{13}H_{13}O_3N$: % calculated: C 67.55, H 5.62, O 20.75, N 6.05. % found: C 67.6, H 5.7, O 20.7, N 6.0.

EXAMPLE 2

5-chloro-7,8,9-trihydro-pyrano[2,3-g]indole-2-carboxylate of methyl

According to the process described in Example 1 and from 16 g ($6.9 \times 10^{-1}$ gram-atoms) of Na dissolved in 600 cm$^3$ of anhydrous methanol, 59 g ($3 \times 10^{-1}$M) of chloroformyl-chroman IIb$_1$ in 250 cm$^3$ of anhydrous methanol and 77 g ($6 \times 10^{-1}$M) of ethyl azidoacetate in 100 cm$^3$ of anhydrous methanol, the azide is isolated which is dissolved in 500 cm$^3$ of xylene and added to 500 cm$^3$ of xylene taken to boiling point. After elimination of the xylene and recrystallisation from ethyl alcohol, 23 g (yield=29%) of expected compound are isolated.

m.p. 238° C.

Analysis $C_{13}H_{12}O_3NCl$: % calculated: C 58.79, O 18.06, N 5.27, Cl 13.34. % found: C 58.7, O 18.3, N 5.3, Cl 13.4.

EXAMPLE 3

5-methoxy-7,8,9-trihydro-pyrano[2,3-g]indole-2-carboxylate of methyl

According to the process described in Example 1, and from 19 g ($8 \times 10^{-1}$ gram-atoms) of Na dissolved in 1250 cm$^3$ of anhydrous methanol, 73 g ($3.8 \times 10^{-1}$M) of methoxyformylchroman IIb$_2$ in 50 cm$^3$ of methanol and 98 g ($7.6 \times 10^{-1}$M) of ethyl azidoacetate in 100 cm$^3$ of methanol, the azide is isolated. After cyclization of the azide in xylene, 38 g (yield=38%) of expected ester are obtained.

m.p.=231° C.

Analysis $C_{14}H_{15}O_4N$: % calculated: C 64.39, H 5.74, O 24.49, N 5.36. % found: C 64.3, H 5.8, O 24.3, N 5.2.

EXAMPLE 4

7,8,9-trihydro-pyrano[2,3-g]indole-2-carboxylic acid

A solution of 17 g ($7.4 \times 10^{-2}$M) of the product of Example 1 and 8.3 g ($1.5 \times 10^{-1}$M) of KOH in 300 cm$^3$ of water is refluxed for 3 hours, 30 minutes. After return to ambient temperature, acidification at 0° C. by 5N hydrochloric acid, the precipitate obtained is filtered, washed with water up to neutrality and recrystallised in an ethanol-water mixture. 13.2 g (yield=83%) of expected acid are isolated.

m.p.=228° C.

Analysis $C_{12}H_{11}O_3N$: % calculated: C 66.38, H 5.06, O 22.09, N 6.44. % found: C 66.5, H 5.2, O 22.1, N 6.4.

EXAMPLE 5

5-chloro-7,8,9-trihydro-pyrano[2,3-g]indole-2-carboxylic acid

When operating is as in accordance with the process of Example 4, and from 22.6 g ($8.5 \times 10^{-2}$M) of product of Example 2 and from 14 g ($2.6 \times 10^{-1}$M) of potassium hydroxide in 300 cm$^3$ of water, 20 g (yield=93%) of expected acid are obtained.

m.p.=308° C.

Analysis $C_{12}H_{10}O_3NCl$: % calculated: C 57.29, H 3.97, O 19.07, N 5.56, Cl 14.09. % found: C 57.1, H 4.0, O 19.2, N 5.6, Cl 13.7.

EXAMPLE 6

5-methoxy-7,8,9-trihydro-pyrano[2,3-g]indole-2-carboxylic acid

According to the process of Example 4 and from 10 g ($3.8 \times 10^{-2}$M) of the product of example 3 in 150 cm$^3$ of methanol and 6.4 g ($1.1 \times 10^{-1}$M) of potassium hydroxide in 15 cm$^3$ of water taken to boiling point for 1 hour 30 mins., 9.3 g (yield=98%) of desired acid are isolated.

m.p.=268° C.

Analysis $C_{13}H_{13}O_4N$: % calculated: C 63.18, H 5.26, O 25.88, N 5.66. % found: C 63.1, H 5.3, O 26.0, N 5.8.

EXAMPLES 7 AND 29

7,8,9-trihydro-pyrano[2,3-g]indole, Example 7 and 5,6,7-trihydro-pyrano[3,2-f]indole, Example 29

120 cm$^3$ of distilled quinoline, 5 g ($2.3 \times 10^{-2}$M) of the product of Example 4 and 80 mg of copper chromite are heated to 190°–195° C. for 7 hours 30 mins. After return to ambient temperature, the catalyst is collected by filtration, the solution is diluted with chloroform and the quinoline is eliminated by washing with 5N hydrochloric acid. The chloroform phase is then washed with water up to neutrality, evaporated and the residue obtained is chromatographed on silicic acid [eluent:-chloroform-hexane (2:1) v/v]. After evaporation of the suitable fractions of elution and recrystallisation from isopropyl ether, 3.3 g (yield=83%) of the desired pyrano[g]indole are isolated; m.p.=115° C. and 0.3 g (yield=7%) of the desired pyrano[f]indole is isolated.

m.p.=97° C.

Analysis $C_{11}H_{11}ON$: % calculated: C 76.32, H 6.35, O 9.23, N 8.08. % found: C 76.3, H 6.5, O 9.3, N 8.0 (Example 7), C 75.7, H 6.5, O 9.2, N 8.0 (Example 29).

EXAMPLE 8

5-chloro-7,8,9-trihydro-pyrano[2,3-g]indole

According to the process of Example 7, and from 9 g ($3.6 \times 10^{-2}$M) of the product of Example 5 and from 0.18 g of copper chromite in 240 cm$^3$ of quinoline, after chromatography on silicic acid (eluent:chloroform) and recrystallisation from a mixture of isopropyl ether and hexane, 5.5 g (yield=74%) of the desired pyrano[2,3-g]indole are isolated.

m.p. 108° C.

Analysis $C_{11}H_{10}ONCl$: % calculated: C 63.65, H 4.81, O 7.70, N 6.74, Cl 17.08. % found: C63.8, H 4.9, O 7.9, N 6.8, Cl 17.2.

EXAMPLE 9

5-methoxy-7,8,9-trihydro-pyrano[2,3-g]indole

According to the process of Example 7, but with a reduced duration of decarboxylation (4 hours), from 12 g ($4.9 \times 10^{-2}$M) of the product of Example 6, 0.24 g of copper chromite and 240 cm$^3$ of quinoline, after chromatography on silicic acid (eluent: chloroform) and recrystallisation from benzene, 6 g (yield=60%) of expected product are isolated.

m.p. 138° C.

Analysis $C_{12}H_{13}O_2N$: % calculated: C 70.96, H 6.40, O 15.74, N 6.89. % found: C 71.0, H 6.4, O 15.8, N 6.8.

EXAMPLE 10

7,8,9-trihydro-pyrano[2,3-g]indole-3-carbaldehyde

In 0.3 g ($2 \times 10^{-3}$M) of phosphorous oxytrichloride in 0.12 g ($1.6 \times 10^{-3}$M) of N,N-dimethylformamide, 10 cm$^3$ of 1,2-dichloroethane then 0.27 g ($1.5 \times 10^{-3}$M) of the product of Example 7 dissolved in 10 cm$^3$ of 1,2-dichloroethane are poured at 5° C. The mixture is maintained at 5° C. for 2 hours 30 mins. then refluxed for 30 mins. After cooling, 1.2 g ($9 \times 10^{-3}$M) of trihydrated sodium acetate dissolved in 10 cm$^3$ of water are added and taken to boiling point for 15 mins. After return to ambient temperature, neutralisation, washing with water, 0.2 g (yield=64%) of the desired aldehyde is obtained—after recrystallisation from ethanol
m.p. 232° C.

Analysis C$_{12}$H$_{11}$O$_2$N: % calculated: C 71.66, H 5.46, O 15.90, N 6.96. % found C 71.6, H 5.4, O 15.9, N 7.0.

EXAMPLE 11

5-chloro-7,8,9-trihydro-pyrano[2,3-g]indole-3-carbaldehyde

From 0.3 g ($2 \times 10^{-3}$M) of phosphorus oxytrichloride, 0.12 g ($1.6 \times 10^{-3}$M) of N,N-dimethylformamide in 10 cm$^3$ of 1,2-dichloroethane and 0.3 g ($1.45 \times 10^{-3}$M) of chlorinated pyrano[g]indole prepared according to Example 8, 0.1 g (yield=29%) of the desired aldehyde, m.p.=214° C., is obtained after chromatography on silicic acid [eluent: chloroform-acetone (3:1) v/v] and recrystallisation from a mixture of benzene and hexane.

Analysis C$_{12}$H$_{10}$O$_2$NCl: % calculated: C 61.18, H 4.24, O 13.57, N 5.94, Cl 15.04. % found: C 59.8, H 4.3, O 13.8.

EXAMPLE 12

5-methoxy-7,8,9-trihydro-pyrano[2,3-g]indole-3-carbaldehyde

According to the process of Example 10 and from 0.3 g ($1.47 \times 10^{-3}$M) of methoxylated pyrano[g]indole of Example 9, 0.11 g (yield=31%) of the expected aldehyde, m.p.=107° C., is isolted after chromatography on silicic acid (eluent: chloroform-acetone (3:1) v/v) and recrystallisation from benzene.

Analysis C$_{13}$H$_{13}$O$_3$N: % calculated: C 67.55, H 5.62, O 20.75, N 6.05. % found: C 67.1, H 5.6, O 20.8, N 6.0.

EXAMPLE 13

3-(7,8,9-trihydro-pyrano[2,3-g]indolyl0-N,N-dimethyl-glyoxamide

In 1 g ($5.7 \times 10^{-3}$M) of pyrano[g]indole prepared according to Example 7 in 25 cm$^3$ of anhydrous ether, is poured—in a current of nitrogen and at 0° C.—a solution of 1 cm$^3$ of oxalyl chloride in 5 cm$^3$ of anhydrous ether. The mixture is maintained for 30 mins. at 0° C. then refluxed for 15 mins; after cooling to 0° C. a solution of dimethylamine is rapidly added until the reaction medium is basic. It is left for 12 hours at ambient temperature, the precipitate which appears is filtered and is recrystallised from methanol. 1.1 g (yield=70%) of the desired derivative are isolated.
m.p.=290° C.

Analysis C$_{15}$H$_5$O$_3$N$_2$: % calculated: C 66.20, H 5.87, N 10.28. % found: C 65.3, H 6.0, N 10.0.

EXAMPLE 14

3-(7,8,9-trihydro-pyrano[2,3-g]indolyl)-N,N-dimethyl-methylamine

A mixture of 0.46 g ($5.7 \times 10^{-3}$M) of 37% w/v formaldehyde, 0.65 g ($5.7 \times 10^{-3}$M) of 40% w/v dimethylamine and 1 g ($5.7 \times 10^{-3}$M) of product of Example 7 in 30 cm$^3$ of methanol, is taken to boiling point for 3 days. After evaporation of the solvent, dissolution of the oily product obtained in ethyl acetate, it is treated with 5N hydrochloric acid, washed with chloroform and the aqueous phase is rendered alkaline by addition of 20% w/v sodium hydroxide. It is then extracted with ether and 0.77 g (yield=58%) of oily product is isolated (free base).

0.8 g ($3.4 \times 10^{-3}$M) of picric acid dissolved in 15 cm$^3$ of ethanol is added at ambient temperature, the reaction mixture is stirred for 12 hours, the precipitate formed is filtered, washed with ethanol and 1.4 g (yield=93%) of picrate is thus obtained
m.p.=160° C.

Analysis C$_{20}$H$_{21}$O$_8$N$_5$: % calculated: C 52.31, H 4.57, O 27.86, N 15.24. % found: C 52.3, H 4.5, O 27.9, N 15.2.

The preparation of the products of Examples 15 and 16 is given in the modi operandi of Examples 17 and 18 respectively.

EXAMPLE 17

5-methoxy-9-oxo-7,8-dihydro-pyrano[2,3-g]indole-2-carboxylate of methyl

To 0.7 g ($3 \times 10^{-2}$ gram-atoms) of Na in 30 cm$^3$ of anhydrous methanol are added 3 g ($1.2 \times 10^{-2}$M) of dioxolan V$_1$ and 3.7 g ($2.9 \times 10^{-2}$M) of ethyl azidoacetate in 10 cm$^3$ of anhydrous methanol. The mixture is maintained for 7 days at 0° C. and extracted with ether. The azide obtained is then dissolved in 70 cm$^3$ of xylene taken to boiling point for 3 hours and the cyclized product thus obtained (Example 15) is treated after dissolution in 50 cm$^3$ of ethanol with 5 cm$^3$ of concentrated hydrochloric acid. The mixture is left for 18 hours and 0.52 g (yield=16%) of the desired ester is isolated after recrystallisation from benzene.
m.p. 188° C.

Analysis C$_{14}$H$_{13}$O$_5$N: % calculated: C 61.12, H 4.72, O 29.06, N 5.08. % found: C 60.9, H 4.6, O 29.2, N 5.1.

EXAMPLE 18

5-chloro-9-oxo-7,8-dihydro-pyrano[2,3-g]indole-2-carboxylate of methyl

From 26 g of dioxolan aldehyde V$_2$ and according to the process described for preparing the preceding product, the product of Example 16 is obtained, after cyclization of the azide (reflux time 8 hours) which, after hydrolysis, gives 15 g (yield=54%) of the desired ester.
m.p.=194° C. (Recrystallisation from benzene).

Analysis C$_{13}$H$_{10}$O$_4$NCl: % calculated: C 55.85, H 3.57, O 22.88, N 5.00, Cl 12.68. % found: C 55.9, H 3.7, O 22.8, N 5.0, Cl 12.8.

EXAMPLE 19

5-methoxy-9-oxo-7,8-dihydro-pyrano[2,3-g]indole-2-carboxylic acid

By using the method of saponification described for the preparation of the product of Example 4 and from 34 g ($1.2 \times 10^{-1}$M) of the product of Example 17 and 14 g ($2.5 \times 10^{-1}$M) of potassium hydroxide in 700 cm³ of water, 30 g (yield=93%) of expected acid are isolated. m.p. 312° C.

Analysis $C_{13}H_{11}O_5N$: % calculated: C 59.80, H 4.21, O 30.62, N 5.36. % found: C 59.0, H 4.2, O 30.8, N 5.3.

EXAMPLE 20

5-chloro-9-oxo-7,8-dihydro-pyrano[2,3-g]indole-2-carboxylic acid

According to the process of Example 19 and from 26 g ($9 \times 10^{-2}$M) of the product of Examples 8, 27 g (yield=90%) of expected acid are obtained. m.p. 227°-230° C.

Analysis $C_{12}H_8O_4NCl$: % calculated: C 54.27, H 3.01, O 24.08, N 5.27. % found: C 54.2, H 3.6, O 24.7, N 5.0.

EXAMPLE 21

5-methoxy-9-oxo-7,8-dihydro-pyrano[2,3-g]indole

According to the method of decarboxylation used for obtaining the pyranoindole of Example 7 and from 31 g ($1.2 \times 10^{-1}$M) of the product of Example 19 and from 0.77 g of copper chromite in 500 cm³ of quinoline, 14 g (yield=54%) of expected product are obtained (m.p. 123° C.) after 13 hours of reaction, chromatography on silicic acid (eluent: chloroform) and recrystallisation from benzene.

Analysis $C_{12}H_{11}O_3N$: % calculated: C 66.38, H 5.06, O 22.09, N 6.44. % found: C 66.4, H 5.1, O 22.2, N 6.3.

EXAMPLE 22

5-methoxy-9-oxo-7,8-dihydro-pyrano[2,3-g]indole-3-carbaldehyde

According to the modi operandi described for the preparation of the product of Example 10 and from 0.4 g ($1.8 \times 10^{-3}$M) of the product of Example 21, 0.19 g (yield=42%) of expected product is obtained (m.p.=236° C.) after chromatography on silicic acid [eluent: cloroform-acetone (3:1) v/v] then recrystallation from a mixture of ethanol-benzene-hexane.

Analysis $C_{13}H_{11}O_4N$: % calculated: C 63.70, H 4.48, O 26.09, N 5.71. % found: C 63.4, H 4.6, O 25.8, N 5.7.

The products of Examples 23 to 28 given in Table I hereinbelow are prepared according to the modi operandi described hereinabove.

EXAMPLE 30

5,6,7-trihydro-pyrano[3,2-f]indole-3-carbaldehyde

According to the process of Example 10 and from 0.2 g ($1.3 \times 10^{-3}$M) of phosphorus oxytrichloride, 0.09 g ($1.2 \times 10^{-3}$M) of N,N-dimethylformamide, 0.2 g ($1.1 \times 10^{-3}$M) of the product of Example 29 and 1 g ($7 \times 10^{-3}$M) of trihydrated sodium acetate, 0.075 g (yield=31%) of expected product (m.p. 195° C.) is isolated after recrystallisation from benzene.

Analysis $C_{12}H_{11}O_2N$: % calculated: C 71.66, H 5.46, O 15.90, N 6.96. % found: C 71.8, H 5.5, O 15.9, N 7.0.

The product of Example 31 given in Table II hereinbelow is prepared according to the modi operandi described hereinabove.

The compounds according to the invention essentially hve anti-ulcerous, anti-inflammatory and antalgic effects. They are particularly useful as anti-ulcerous, anti-inflammatory and antalgic agents in the treatment of ulcers, pain and inflammations. Certain products further present anti-aggregating and anti-thrombotic effects useful in the treatment of diseases associated with circulatory disorders.

The pharmacological tests carried out particularly with regard to toxicity, the ulcers provoked by aspirin and serotonin, and the anti-inflammatory and antalgic effects, are summarised hereinafter. The methods used are recalled hereinafter.

ULCER PROVOKED BY ASPIRIN

The experiment is carried out on male Wistar rats weighing 180 to 200 g.

At t=0 the rats are made to fast and a first administration of the product to be tested, at a dose of 100 mg/kg, is made IP. At t=18 hours, 2 ml of an ulcer-forming suspension with 192 mg of aspirin/kg are administered per os then a second IP administration of the product to be tested, at a dose of 100 mg/kg, is made.

At t=22 hours, the animals are sacrificed and the ulcers are marked as follows:
small punctiform ulcers: mark 1
more extensive ulcers: mark 3
very extensive or very deep ulcers: mark 9

The results relative to the inhibition of the ulcers provoked by aspirin are given in Table III hereinafter.

ULCER PROVOKED BY SEROTONIN

The technique used is the one described by Hashizume, in Arch. Int. Pharmacodyn. 236, 96–108, (1978).

The experiment is carried out on 3 batches of male Sprague-Dawley rats. Each batch includes 20 animals.

The first batch constitutes the controls, the second is treated with Carbenoxolone, the third is treated with the product to be tested.

The animals are made to fast 24 hours before the experiment.

At t=0,
the product to be tested is administered by the IP route to the third batch,
100 mg/kg of Carbenoxolone are administered per os to the second batch.

At t=+10 mins., a sub-cutaneous injection is made of serotonin at 60 mg/kg in the three batches.

At t=+250 mins., the animals are sacrificed. The stomachs are removed and spread out and the ulcers are marked as follows:
small ulcer +=1
average ulcer ++=3
large ulcer +++=9

The results relative to the inhibition of the ulcers provoked by serotonin are given in Table IV hereinbelow with the doses of the products tested.

The techniques relative to the anti-inflammatory effects (oedema caused by carragenine) and antalgic effects (cramping) which were used are the conventional techniques described in the prior art. The results obtained are given in Table III hereinbelow.

Table III hereinbelow deals with the $LD_{50}$ and with the inhibition of the ulcers caused by aspirin, the inhibition of the oedema provoked by carragenine and cramping (the products to be tested being, in the latter two cases, administered by the IP route at a dose equal to one tenth of the $LD_{50}IP$).

According to the invention, a therapeutic composition is recommended, characterised in that it contains, in association with a physiologically acceptable excipient, a pharmaceutically effective dose of a pyranoindole derivative according to the invention or one of its non-toxic acid addition salts.

tered by the oral route divided 4 or 5 times a day, for at least 2 to 3 weeks.

TABLE I

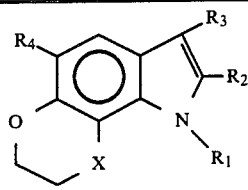

| Example | Code No | X | $R_1$ | $R_2$ | $R_3$ | $R_4$ | Melting point °C. |
|---|---|---|---|---|---|---|---|
| 1 | — | $CH_2$ | H | $COOCH_3$ | H | H | 163 |
| 2 | — | $CH_2$ | H | $COOCH_3$ | H | Cl | 238 |
| 3 | — | $CH_2$ | H | $COOCH_3$ | H | $OCH_3$ | 231 |
| 4 | 231 | $CH_2$ | H | COOH | H | H | 228 |
| 5 | 258 | $CH_2$ | H | COOH | H | Cl | 308 |
| 6 | 336 | $CH_2$ | H | COOH | H | $OCH_3$ | 268 |
| 7 | 275 | $CH_2$ | H | H | H | H | 115 |
| 8 | 338 | $CH_2$ | H | H | H | Cl | 108 |
| 9 | 337 | $CH_2$ | H | H | H | $OCH_3$ | 138 |
| 10 | — | $CH_2$ | H | H | CHO | H | 232 |
| 11 | — | $CH_2$ | H | H | CHO | Cl | 214 |
| 12 | — | $CH_2$ | H | H | CHO | $OCH_3$ | 107 |
| 13 | — | $CH_2$ | H | H | $CO-CON(CH_3)_2$ | H | 290 |
| 14 | 333 | $CH_2$ | H | H | $CH_2N(CH_3)_2$ | H | — (a) |
| 15 | — | $O\text{-}CH\text{-}O$ (methylenedioxy) | H | $COOCH_3$ | H | $OCH_3$ | — (b) |
| 16 | — | $O\text{-}CH\text{-}O$ (methylenedioxy) | H | $COOCH_3$ | H | Cl | — (b) |
| 17 | — | CO | H | $COOCH_3$ | H | $OCH_3$ | 188 |
| 18 | — | CO | H | $COOCH_3$ | H | Cl | 194 |
| 19 | 266 | CO | H | COOH | H | $OCH_3$ | 312 |
| 20 | — | CO | H | COOH | H | Cl | 227–230 |
| 21 | 205 | CO | H | H | H | $OCH_3$ | 123 |
| 22 | — | CO | H | H | CHO | $OCH_3$ | 236 |
| 23 | 598 | C=NOH | H | H | H | $OCH_3$ | 222 |
| 24 | 599 | CHOH | H | H | H | $OCH_3$ | 147 |
| 25 | — | $CHNH_2$ | H | H | H | $OCH_3$ | (b) |
| 26 | — | CO | H | H | $CH_2N(CH_3)_2$ | $OCH_3$ | 121 |
| 27 | — | $CH_2$ | $(CH_2)_3N(CH_3)_2$ | H | H | Cl | 69 |
| 28 | — | $CH_2$ | $CH_3$ | H | H | Cl | 152 |

Note:
(a) free base is an oily product, corresponding picrate melts at 160° C.;
(b) oil.

In clinic, excellent results have been obtained in man, in the treatment of ulcers with the products of Examples 7, 8, 14, 19, 21 and 23, in the treatment of pain with the product of Example 6, and in the treatment of oedemas with the products of examples 4, 5, 9 and 24.

The dosage recommended for the treatment of gastric or duodenal ulcers, in the male adult, is 50 mg to 1500 mg per day, by oral administration. Such a dose may be divided and taken 2 to 5 times per day. 100 mg to 1000 mg of active ingredient are preferably adminis-

TABLE II

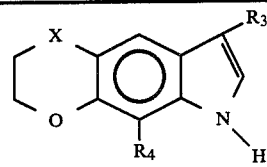

| Example | Code No | X | $R_3$ | $R_4$ | Melting point °C. |
|---|---|---|---|---|---|
| 29 | — | $CH_2$ | H | H | 97 |
| 30 | — | $CH_2$ | CHO | H | 195 |

TABLE III
| Example | Code No | DL$_{50}$ mg/kg I.P. | Aspirine induced ulcer % inhibition | Carragheenine oedema % inhibition | Cramping % inhibition |
|---|---|---|---|---|---|
| 21 | 205 | 600 | 60 | 49 | 37 |
| 4 | 231 | 600 | 11 | 35 | 36 |
| 5 | 258 | 300 | 28 | 30 | 35 |
| 7 | 275 | 750 | 46 | — | 14 |
| 19 | 266 | >1000 | 49 | — | — |
| 14 | 333 | 180 | 47.5 | 22 | 67 |
| 6 | 336 | >800 | 23 | — | 66 |
| 9 | 337 | 650 | 51 | 39 | 41 |
| 8 | 338 | 900 | 42.5 | 33 | 26 |
| 23 | 598 | (DL$_o$ > 800) | 40 | 52 | 51 |
| 24 | 599 | 1000 | — | 40 | 60 |
TABLE II-continued
| Example | Code No | X | R$_3$ | R$_4$ | Melting point °C. |
|---|---|---|---|---|---|
| 31 | — | CH$_2$ | H | Cl | 117 |
TABLE IV
| Example | Code No | Dosis mg/kg IP | Serotonine ulcer % inhibition |
|---|---|---|---|
| 7 | 275 | 75 | 64 |
| 8 | 338 | 45 | 75 |
| 21 | 205 | 60 | 87 |
| 23 | 598 | 92 | 52 |
| Carbenoxolone | — | 60 | 64 |
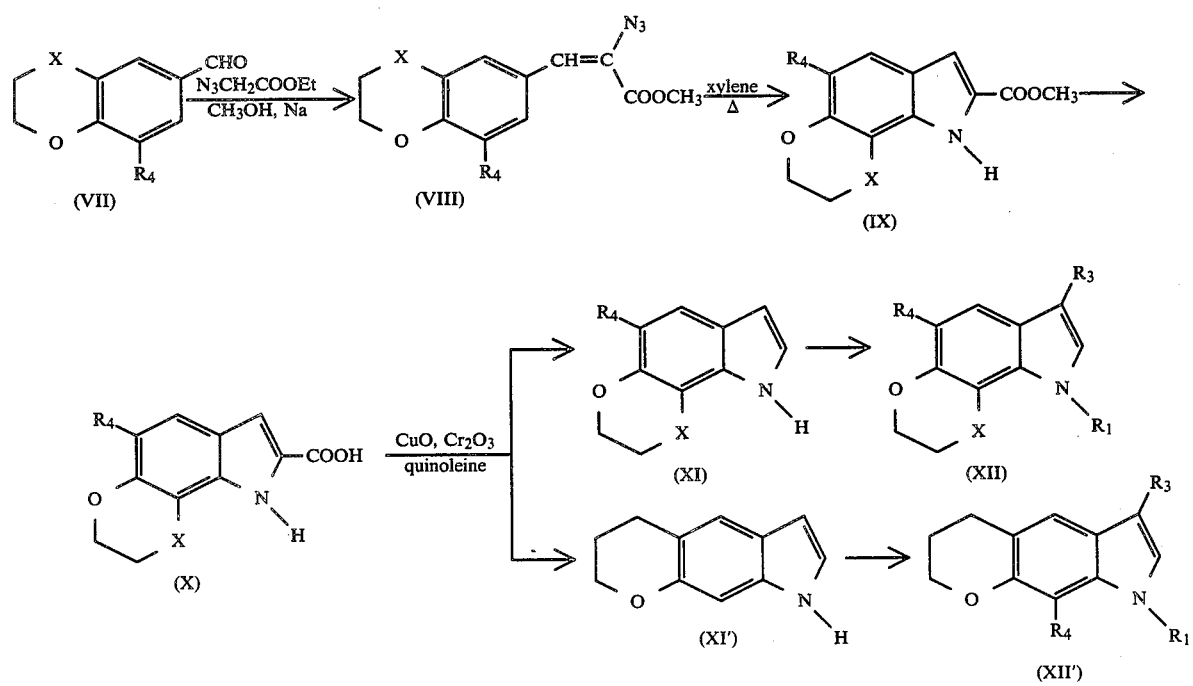
DIAGRAM 1

DIAGRAM 2

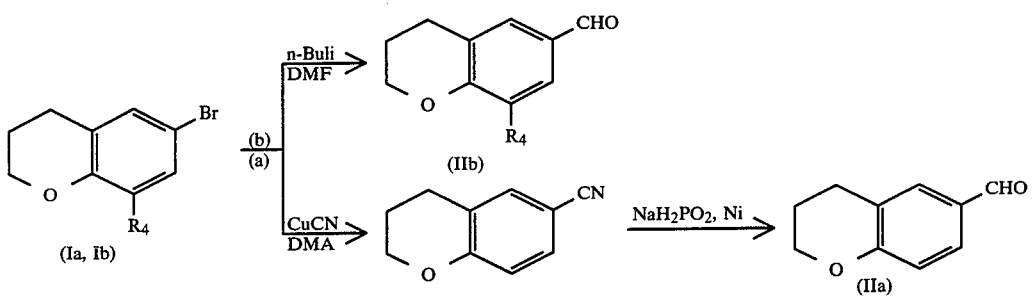

(a) R4 = H
(b) R4 ≠ H

DIAGRAM 3

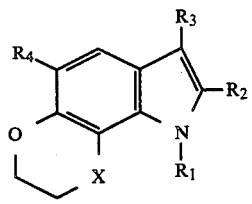

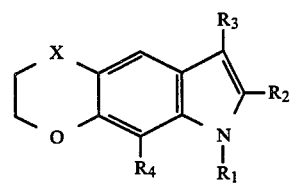

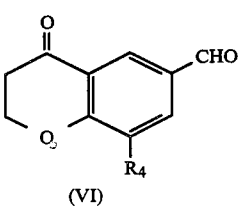

What is claimed is:

1. Pyranoindole compounds selected from the group consisting of:
   (i) pyrano[2,3-g]indoles of the formula: and

[structure with R3, R4, R2, X, N-R1]

(ii) pharmaceutically acceptable acid addition salts thereof:
   in which:
   X represents a group $CH_2$, CHOH, or CO;
   $R_1$ represents an atom of hydrogen, a lower alkyl group, or an aminoalkylene group —$(CH_2)_n$—NR'R" (in which n is a whole number between 1 and 4 and R' and R" which are identical or different, each represent H or a lower alkyl);
   $R_2$ represents an atom of hydrogen;
   $R_3$ represents an atom of hydrogen, a CHO group, CO—CONR'R" (in which n, R', R" are defined as hereinabove), or $(CH_2)_n$NH'R (in which R' and R" are $CH_3$ and n is 1); and
   $R_4$ represents an atom of hydrogen, halogen, or a lower ($C_1$-$C_4$) alkoxy.

2. Pyranoindole compounds selected from the group consisting of:
   (i) the pyrano[3,2-f]indoles of the formula; and

[structure I'o with X, R3, R2, R4, N-R1]

(ii) pharmaceutically acceptable acid addition salts thereof:
   in which:
   X represents $CH_2$;
   $R_1$ represents an atom of hydrogen;
   $R_2$ represents an atom of hydrogen;
   $R_3$ represents an atom of hydrogen, or a CHO group; and
   $R_4$ represents an atom of hydrogen, or an atom of halogen.

3. The compound of claim 1 which is 5-methoxy-7,8,9-trihydro-pyrano[2,3-g]indole.

4. The compound of claim 1, which is 3-(7,8,9-trihydro-pyrano[2,3-g]indolyl)-N,N-dimethylmethylamine and its acid addition salts.

5. The compound of claim 1, which is 5-methoxy-9-oxo-7,8-dihydro-pyrano[2,3-]indole.

6. The compound of claim 2, which is 5,6,7-trihydro-pyrano[3,2-f]indole-3-carboxaldehyde.

7. A therapeutical composition useful as anti-ulcer agents containing, in asociation with a physiologically acceptable excipient, at least one pyrano-indole compound or one of its pharmaceutically acceptable acid addition salts according to claim 1.

8. A therapeutical composition useful as anti-ulcer agents containing, in association with a physiologically acceptable excipient, at least one pyrano-indole compound or one of its pharmaceutically acceptable acid addition salts according to claim 2.

* * * * *